United States Patent
Bessette

(10) Patent No.: US 6,858,653 B1
(45) Date of Patent: Feb. 22, 2005

(54) PESTICIDAL COMPOSITIONS CONTAINING PLANT ESSENTIALS OILS AGAINST TERMITES

(75) Inventor: Steven M. Bessette, Brentwood, TN (US)

(73) Assignee: EcoSmart Technologies, Inc., Franklin, TN (US)

( * ) Notice: Subject to any disclaimer, the term of this patent is extended or adjusted under 35 U.S.C. 154(b) by 0 days.

(21) Appl. No.: 09/604,157

(22) Filed: Jun. 27, 2000

Related U.S. Application Data

(60) Provisional application No. 60/140,846, filed on Jun. 28, 1999.

(51) Int. Cl.$^7$ .............................................. A01N 31/08
(52) U.S. Cl. ...................... 514/730; 424/405; 424/406; 424/DIG. 11; 514/544
(58) Field of Search ................................ 424/405, 406, 424/DIG. 11; 514/724, 730, 720, 544

(56) References Cited

U.S. PATENT DOCUMENTS

| | | | |
|---|---|---|---|
| 1,514,377 A | * 11/1924 | Dow et al. ................... | 514/730 |
| 4,075,071 A | 2/1978 | Kirschbaum | |
| 4,446,153 A | * 5/1984 | Yang .......................... | 514/730 |
| 4,833,158 A | * 5/1989 | Twydell et al. ............. | 514/616 |

FOREIGN PATENT DOCUMENTS

| | | |
|---|---|---|
| DE | 4231045 | 3/1994 |

OTHER PUBLICATIONS

Vapour Toxicity—Sharma et al insect Sci Applic. to Termite vol. 15 #4/5 PP 495–498, 1994.*

Lin, Tien–Shu, et al., "The Effects Of Cinnamonium supp. Oils On The Control Of The Termite Coptotermes Formosanus Shiraki", Bullet Tawian Foresty Res., Inst. vol. 10, No. 4, 1995, pp. 459–464.

Derwent Publications Ltd., "Anti Terminte Preserve Composition Wood Comprise Terpinolene Alpha Terpineol Acetate Oil Wood Impregnate Fine Particel Synthetic Resin Aqueous Surfactant", Aug. 4, 1998, Abstract.

Cornelius, M. L. et al., Toxicity Of Monoterpeniods And Other Natural Products To The Formosan Subterranean Termite (Isoptera: Rhinotermitidae), Journal of Economic Entomology, vol. 90, No. 2, 1997, pp. 320–325.

Sharma, R.N. et al., "Vapour Toxicity and Repellency of Some Oils and Terpenoids to the Termite, Odontotermes Brunneus", Insect Sci. Applic., vol. 90, No. 2, 1994, pp. 495–498.

Asada, T., et al., "Insecticidal and Antifungal Activity in Hinoki–Asunaro Leaf Oil", Wood Res. Inst., vol. 35, No. 9, 1989, pp. 851–855.

Derwnt Publications, Ltd., "Fire Paint Produce Mix REsin Emulsion Fire REtard Terpenic Animal Repel Prolong Effect Rat Termite", Showa Electric Wire Co., Ltd., Jan. 31, 1991, Abstract.

Akhtar, M.S. et al., "Responses of *Coptotermes heimi* (Wasmann) (Isoptera) to Woods, Wood Extracts and Essential Oils of Timbers", Material Und ORganismen, vol. 16, No. 3, 1981, pp. 199–206.

Masaki, S., "Insect Repellents Containing Natureal Essential Oils Against Termites", Chemical Abstracts, vol. 125, No. 7, Aug. 12, 1996.

* cited by examiner

*Primary Examiner*—Neil S. Levy
(74) *Attorney, Agent, or Firm*—Nixon & Vanderhye P.C.

(57) ABSTRACT

Pesticidal compositions for the control of mites in stored food products containing one or more plant essential oils. In addition, the present invention is directed to a method for controlling mites from accessing stored food products by applying a pesticidally-effective amount of the above pesticidal compositions to a locus where pest control is desired.

4 Claims, No Drawings

PESTICIDAL COMPOSITIONS CONTAINING PLANT ESSENTIALS OILS AGAINST TERMITES

CROSS REFERENCE TO RELATED APPLICATION

This application claims the benefit of U.S. Provisional Application Ser. No. 60/140,846, filed Jun. 28, 1999, the entire disclosure of which is incorporated herein by reference.

FIELD OF THE INVENTION

The present invention relates, in general, to pesticidal compositions containing plant essential oils and/or derivatives thereof against termites. In one aspect, the present invention relates to pesticidal compositions containing one or more plant essential oils and/or derivatives thereof to be used as a contact pesticide against termites. In a further aspect, the present invention relates to a method for controlling termites by the application of pesticidally effective amounts of the pesticidal compositions to a locus where pest control is desired.

BACKGROUND OF THE INVENTION

Pests (invertebrates, insects, arachnids, larvae thereof, etc.) are annoying to humans for a myriad of reasons. They have annually cost humans billions of dollars in crop losses and in the expense of keeping them under control. For example, the losses caused by pests in agricultural environments include decreased crop yield, reduced crop quality, and increased harvesting costs.

Over the years, synthetic chemical pesticides have provided an effective means of pest control. For example, one approach teaches the use of complex, organic insecticides, such as disclosed in U.S. Pat. Nos. 4,376,784 and 4,308,279. Other approaches employ absorbent organic polymers for widespread dehydration of the insects. See, U.S. Pat. Nos. 4,985,251; 4,983,390; 4,818,534; and 4,983,389. Use of inorganic salts as components of pesticides has also been tried, as disclosed in U.S. Pat. Nos. 2,423,284 and 4,948,013, European Patent Application No. 462 347, Chemical Abstracts 1 19(5):43357q (1993) and Farm Chemicals Handbook, page c102 (1987).

However, it has become increasingly apparent that the widespread use of synthetic chemical pesticides has caused detrimental environmental effects that are harmful to humans and other animals. For instance, the public has become concerned about the amount of residual chemicals that persist in food, ground water and the environment, and that are toxic, carcinogenic or otherwise incompatible to humans, domestic animals and/or fish. Moreover, some target pests have even shown an ability to develop immunity to many commonly used synthetic chemical pesticides. In recent times, regulatory guidelines have encouraged a search for potentially less dangerous pesticidal compositions via stringent restrictions on the use of certain synthetic pesticides. As a result, elimination of effective pesticides from the market has limited economical and effective options for controlling pests. As an alternative, botanical pesticides are of great interest because they are natural pesticides, i.e., toxicants derived from plants that are safe to humans and the environment With respect to termites, the safety issue is even more critical. The most effective termiticide of the past thirty years, chlordane, has recently been banned by the U.S. Environmental Protection Agency because of its toxicity to mammals and the environment, and the other alternatives are also under review. Most termiticides in use today are limited in usage and heavily regulated by government agencies. Since termites destroy wood and affect the structural integrity of buildings, homes and other facilities, and termites are spreading into expanded areas, the use of termiticides is always under review by many groups, including but not limited to state governmental units, environmental groups, consumer safety groups, and consumer advocate groups. The danger to both the environment and persons is the dominant issue with the current use of termiticides for both dry wood and subterranean termites. For subterranean termites in particular, it is common to pretreat the ground beneath the concrete slab or foundation, to protect against termite infestation. Unfortunately, in addition to the negative exposure to the environment of toxic chemicals, this single treatment is not totally effective. Moreover, subsequent treatments are prohibited by law in most jurisdictions due to various toxicity concerns unless an infestation is found, at which point it is usually too late to prevent damage to the structure. It would be desirable to provide a safe method of retreatment to supplement the pretreatment and provide an additional layer of protection. In addition, it would be desirable to provide a repellent barrier of protection under the ground to avoid the structure entirely. It would also be desirable to treat the structure or the concrete slab during construction to provide a repellent/pesticidal barrier of protection. It would also be desirable to incorporate the pesticidal composition into the concrete slab itself, as opposed to treating the ground beneath the concrete slab. This would preserve the pesticidal properties of the pesticidal compositions and minimize environmental impact.

Accordingly, there is a great need for novel pesticidal compositions, containing no pyrethrum, synthetic pyrethroids, chlorinated hydrocarbons, organo phosphates, carbamates and the like, to be used against termites. In addition, there is a need for a method of treating the structure and foundation to kill and repel termites.

SUMMARY OF THE INVENTION

A primary object of the present invention is to provide novel pesticidal compositions for use against termites.

Another object of the invention is to provide novel pesticidal compositions containing one or more plant essential oils and/or derivatives thereof, natural or synthetic, as a contact pesticide in the household against termites.

It is also an object of the present invention to provide a method of treating the structure, foundation and soil to kill and repel termites.

It is also an object of the present invention to provide a pesticidal composition and method for mechanically, physiologically and/or neurally controlling termites.

It is a further object to provide a safe, non-toxic pesticidal composition and method that will not harm mammals or the environment.

It is still another object to provide a pesticidal composition and method that has a pleasant scent or is unscented, and that can be applied without burdensome safety precautions.

It is still another object to provide a pesticidal composition and method as described above which can be inexpensively produced or employed.

It is yet another object of the invention to provide a pesticidal composition and method to which pests cannot build immunity and/or resistance.

The above and other objects are accomplished by the present invention which is directed to pesticidal compositions comprising plant essential oils and/or derivatives thereof, natural or synthetic, in admixture with suitable carriers. In addition, the present invention is directed to a method for controlling termites by applying a pesticidally-effective amount of the above pesticidal compositions to the structure, foundation or soil.

Additional objects and attendant advantages of the present invention will be set forth, in part, in the description that follows, or may be learned from practicing or using the present invention. The objects and advantages may be realized and attained by means of the instrumentalities and combinations particularly recited in the appended claims. It is to be understood that the foregoing general description and the following detailed description are exemplary and explanatory only and are not to be viewed as being restrictive of the invention, as claimed.

DETAILED DESCRIPTION OF PREFERRED EMBODIMENTS

All patents, patent applications and literatures cited in this description are incorporated herein by reference in their entirety. In the case of inconsistencies, the present disclosure, including definitions, will prevail.

In one embodiment, the present invention provides a pesticidal composition comprising, in admixture with a suitable carrier and optionally with a suitable surface active agent, comprising one or more plant essential oil compounds and derivatives thereof, natural or synthetic, including racemic mixtures, enantiomers, diastereomers, hydrates, salts, solvates and metabolites, etc.

Each plant essential oil or derivative thereof, comprises a monocyclic, carbocyclic ring structure having six-members and substituted by at least one oxygenated or hydroxyl functional moiety. Examples of plant essential oils encompassed within the present invention, include, but are not limited to, members selected from the group consisting of aldehyde C16 (pure), α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol (cineole), eugenol, isoeugenol, galaxolide, geraniol, guaiacol, ionone, menthol, methyl anthranilate, methyl ionone, methyl salicylate, α-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen4-ol, terpinyl acetate, 4-tert butylcyclohexyl acetate, thyme oil, thymol, metabolites of trans-anethole, vanillin, ethyl vanillin, and the like. As these plant essential oil compounds are known and used for other uses, they may be prepared by a skilled artisan by employing known methods.

For example, in a preferred embodiment, the present invention is directed to a pesticidal composition for controlling termites comprising a mixture of plant essential oils which include α-terpineol, 2-phenyl ethyl alcohol, 2-phenyl ethyl propionate and benzyl alcohol with a suitable solvent carrier. Data below shows that this embodiment is highly effective, i.e. exhibited excellent control against termites.

It will be appreciated by the skilled artisan that the pesticidal compositions of the present invention unexpectedly exhibit excellent pesticidal activities using one or more U.S. F.D.A. approved plant essential oils, in lieu of conventional pesticides which are not safe for use in households, structures, and underground. Without wishing to be bound by the following theories, it is believed that plant essential oils antagonize a pest's nerve receptors or may act as Phase I and/or Phase II drug metabolizing enzyme inhibitors. Alternatively, plant essential oils may act via an alternative mode of action. The plant essential oils may act as agonists or antagonists against the octopamine receptors that are distinct to invertebrates. In any event, the net effect of the toxicity and action of the inventive composition disclosed herein is heretofore unknown and unexpected.

Use of pesticidal compositions of the present invention generally results in 100% mortality on contact. As such, they are advantageously employed as pesticidal agents in uses such as, without limitation, households, soil pretreatments, soil retreatments, concrete, wood, professional pest control, underwater or submerged application, solid treatment, and soil incorporation application.

With respect to soil, the pesticidal compositions resist weathering which includes wash-off caused by rain, decomposition by ultra-violet light, oxidation, or hydrolysis in the presence of moisture or, at least such decomposition, oxidation and hydrolysis as would materially decrease the desirable pesticidal characteristic of the pesticidal compositions or impart undesirable characteristics to the pesticidal compositions. The pesticidal compositions are so chemically inert that they are compatible with substantially any other constituents of pest control, and they may be used in the soil, upon the seeds, or the roots of plants without injuring either the seeds or roots of plants. They may also be used in combination with other pesticidally active compounds.

The term "carrier" as used herein means an inert or fluid material, which may be inorganic or organic and of synthetic or natural origin, with which the active compound is mixed or formulated to facilitate its application to the container or carton or other object to be treated, or its storage, transport and/or handling. In general, any of the materials customarily employed in formulating pesticides, herbicides, or fungicides, are suitable. The inventive pesticidal compositions of the present invention may be employed alone or in the form of mixtures with such solid and/or liquid dispersible carrier vehicles and/or other known compatible active agents such as other pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The pesticidal compositions of the present invention can be formulated or mixed with, if desired, conventional inert pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

Formulations containing the pesticidal compositions of the present invention may be prepared in any known manner, for instance by extending the pesticidal compositions with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the pesticidal compositions of the present invention. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

Liquid concentrates may be prepared by dissolving a composition of the present invention with a solvent and dispersing the pesticidal compositions of the present inventions in water with the acid of suitable surface active emulsifying and dispersing agents. Examples of conventional carrier vehicles for this purpose include, but are not limited to, aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g. kaolins, clays, vermiculite, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.).

Surface-active agents, i.e., conventional carrier vehicle assistants, that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which acts carriers for the pesticide. These finely divided solids preferably have an average particle size of less than about 50 microns. A typical dust formulation useful for controlling insects contains 1 part of pesticidal composition and 99 parts of diatomaceous earth or vermiculite. Granules may comprise porous or nonporous particles. The granule particles are relatively large, a diameter of about 400–2500 microns typically. The particles are either impregnated or coated with the inventive pesticidal compositions from solution. Granules generally contain 0.05–15%, preferably 0.5–5%, active ingredient as the pesticidally-effective amount. Thus, the contemplated are formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

In commercial applications, the present invention encompasses carrier composition mixtures in which the pesticidal compositions are present in an amount substantially between about 0.01–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The pesticidal compositions can also be used in accordance with socalled ultra-low-volume process, i.e. by applying such compounds or by applying a liquid composition containing the same, via very effective atomizing equipment, in finely divided form, e.g. average particle diameter of from 50–100 microns, or even less, i.e. mist form, for example by airplane crop spraying techniques. In this process it is possible to use highly concentrated liquid compositions with said liquid carrier vehicles containing from about 20 to 95% by weight of the pesticidal compositions or even the 100% active substances alone, e.g. about 20–100% by weight of the pesticidal compositions. The concentration in the liquid concentrate will usually vary from about 10 to 95 percent by weight and in the solid formulations from about 0.5 to 90 percent by weight.

Furthermore, the present invention encompasses methods for killing, combating or controlling pests, which comprises applying to at least one of correspondingly (a) such pests and (b) the corresponding habitat thereof, i.e. the locus to be protected, e.g. to the structure, foundation, or soil, a correspondingly combative, a pesticidally effective amount, or toxic amount of the particular pesticidal compositions of the invention alone or together with a carrier as noted above. The instant formulations or compositions may be applied in any suitable usual manner, for instance by spraying, atomizing, vaporizing, scattering, dusting, watering, squirting, sprinkling, pouring, fumigating, and the like. The method for controlling termites comprises applying the inventive composition, ordinarily in a formulation of one of the aforementioned types, to a locus or area to be protected from the termites, such as the structure, foundation or soil. The compound, of course, is applied in an amount sufficient to effect the desired action. This dosage is dependent upon many factors, including the targeted pest, the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected-i.e., the dosage with which the pest comes in contact-is of the order of 0.001 to 5.0% based on the total weight of the formulation, though under some circumstances the effective concentration will be as little as 0.0001% or as much as 20%, on the same basis.

The pesticidal compositions and methods of the present invention are effective against different species of termites and it will be understood that the termites exemplified and evaluated in the working Examples herein is representative of such a wider variety.

The composition and method of the present invention will be further illustrated in the following, non-limiting Examples. The Examples are illustrative of various embodiments only and do not limit the claimed invention regarding the materials, conditions, weight ratios, process parameters and the like recited herein.

EXAMPLE 1

Pesticidal Effects of Plant Essential Oils against the Drywood Termite

A variety of plant essential oils and mixtures thereof were evaluated for contact toxicity against the drywood termite. The plant essential oils were dissolved in acetone at a 1:18 ratio by volume of plant essential oil to acetone. Approximatley 0.5 ml of each test substance was applied to 9-cm diam. glass petri dishes and allowed to dry for one half-hour. Five to ten termites were then exposed to the petri dishes and observed for mortality one hour post treatment. A control dish with just acetone was also monitored.

| Test Chemical | % Mortality-1 hr |
|---|---|
| Control | 0 |
| Benzyl acetate | 100 |
| Eugenol | 100 |
| V-1924 (benzyl alcohol, α-terpineol, 2-phenyl ethyl propionate, 2-phenyl ethyl alcohol) | 100 |
| α-terpineol | 100 |
| 2-phenyl ethyl propionate | 100 |
| V-3052 (eugenol, α-terpineol, cinnamic alcohol) | 100 |
| Benzyl alcohol | 100 |
| Thymol | 100 |
| Trans-anethole | 100 |

This data clearly demonstrates that plant essential oils may be used as a safe and effective alternative pesticide for control of termites. The plant essential oils demonstrated rapid speed of action and total control.

As can be seen from the above discussion, the pesticidal combinations of active compounds according to the present invention are markedly superior to known pesticidal agents/active compounds conventionally used for control of termites.

Although illustrative embodiments of the invention have been described in detail, it is to be understood that the present invention is not limited to those precise embodiments, and that various changes and modifications can be effected therein by one skilled in the art without departing from the scope and spirit of the invention as defined by the appended claims.

What is claimed is:

1. A method for killing or controlling termites, which comprises:

applying to a termite or a locus where control of termites is desired, a pesticidally-effective amount of a composition comprising an active ingredient and a pesticidally-acceptable carrier, wherein the active ingredient is benzyl alcohol.

2. The method of claim 1, wherein the active ingredient further comprises methyl salicylate.

3. The method of claim 1, wherein the active ingredient further comprises phenyl ethyl propionate.

4. The method of claim 1, where the active ingredient further comprises eugenol.

* * * * *